US006096947A

United States Patent [19]
Jayne et al.

[11] Patent Number: 6,096,947
[45] Date of Patent: Aug. 1, 2000

[54] METHODS FOR IMPROVING TRANSFORMATION EFFICIENCY

[75] Inventors: Susan Jayne; Eric Barbour, both of Des Moines; Terry Meyer, Urbandale, all of Iowa

[73] Assignee: Pioneer Hi-Bred International, Inc., Johnston, Iowa

[21] Appl. No.: 09/003,287

[22] Filed: Jan. 6, 1998

Related U.S. Application Data

[60] Provisional application No. 60/035,560, Jan. 14, 1997.

[51] Int. Cl.$^7$ ............................. C12N 5/04; C12N 15/11; C12N 15/82; A01H 5/00; A01H 5/10
[52] U.S. Cl. ...................... 800/300; 800/288; 800/300.1; 800/320; 800/320.1; 800/320.3; 435/69.1; 435/413; 435/418; 435/419; 435/440; 435/468; 536/23.6; 536/23.7
[58] Field of Search ................................. 435/69.1, 410, 435/412, 413, 418, 419, 430, 440, 468; 536/23.6, 23.7; 800/278, 288, 295, 300, 300.1, 320.1, 320.3, 320

[56] References Cited

U.S. PATENT DOCUMENTS 5,380,831   1/1995   Adang et al. ........................ 536/23.71

FOREIGN PATENT DOCUMENTS

WO96/27675   9/1996   WIPO ............................. C12N 19/82

OTHER PUBLICATIONS

Ye et al, Plant Cell Rep., vol. 15, pp. 479–483, 1996.
Shimada et al, Nucl. Acids Res., vol. 19, pp. 983–995, 1991.
Omirulleh et al, Plant Mol. Biol., vol. 21, pp. 415–428, 1993.
Svab et al, Proc. Natl. Acad. Sci. USA, vol. 90, pp. 913–917, 1993.
Galbraith et al, Meth. Cell Biol., vol. 50, pp. 3–14, 1995.
Ortiz et al., "Hygromycin Resistance as an Efficient Selectable Marker for Wheat Stable Transformation", *Plant Cell Reports*, 15:877–881 (1996).
Chamberlain et al., "The Use of the Emu Promoter with Antibiotic and Herbicide Resistance Genes for the Selection of Transgenic Wheat Callus and Rice Plants", *Aust. J. Plant Physiol.*, 21:95–112 (1994).
Wohlleben et al., Nucleotide Sequence of the Phosphinothricin N–acetyltransferase gene from *Streptomyces viridochromogenes* TÜ494 and Its Expression in *Nicotiana tabacum* Gene, 70:25–37 (1998).
Perez et al., "Phleomycin Resistance as a Dominant Selectable Marker for Plant Cell Transformation", *Plant Molecular Biology*, 13:365–373 (1989).
Li et al., "Agronomic Trait Evaluation of Field–Grown Transgenic Rice Plants Containing the Hygromycin Resistance Gene and the Maize Activator Element", *Plant Science*, 108:219–227 (1995).
David Bradley, "Genetic Weeding and Feeding for Tobacco Plants", New Scientest, Jan. 4, 1992, p. 11.

Chiu et al., "Engineered GFP as a Vital Reporter in Plants", *Current Biology*, vol. 6, No. 3:325–330 (1996).
Maier–Greiner et al., "Isolation and Properties of a Nitrile Hydratase from the Soil Fungus *Myrothecium verrucaria* That is Highly Specific for the Fertilizer Cyanamide and Cloning of Its Gene", *Proc. Natl. Acad. Sci.*, 88:4260–4264, (May 1991).
Kain et al., "Green Fluorescent Protein as a Reporter of Gene Expression and Protein Localization", *BioTechniques*, 19:650–655 (Oct. 1995).
David Bradley, "Genetic Weeding and Feeding for Tobacco Plants", New Scientest, Jan. 4, 1992, p. 11.
Goddijn et al., "A Chimaeric Tryptophan Decarboxylase Gene as a Novel Selectable Marker in Plant Cells", *Plant Molecular Biology*, 22:907–912 (1993).
Perlak et al., "Modification of the Coding Sequence Enhances Plant Expression of Insect Control Protein Genes", *Proc. Natl. Acad. Sci. USA*, 88:3324–3328 (Apr. 1991).
Perl et al., "Bacterial Dihydrodipicolinate Synthase and Desensitized Aspartate Kinase: Two Novel Selectable Markers for Plant Transformation", *Bio/Technology*, 11:715–718 (Jun. 1993).
Sagnard et al., "Selection of Transgenic Flax Plants is Facilitated by Spectinomycin", *Transgenic Research*, 5:131–137 (1996).
Meijer et al., "Transgenic Rice Cell Lines and Plants: Expression of Transferred Chimeric Genes", *Plant Molecular Biology*, 16:807–820 (1991).
Toki et al., "Expression of a Maize Ubiquitin Gene Promoter–bar Chimeric Gene in Transgenic Rice Plants", *Plant Physiol.*, 100:1503–1507 (1992).
Fennoy et al., "Synonymous Codon Usage in *Zea mays* L. Nuclear Genes Is Varied by Levels of C and G–Ending Codons", *Nucleic Acids Research*, vol. 21, No. 23:5294–5300.
Murray et al., "Codon Usage in Plant Genes", *Nucleic Acids Research*, 17:477–498.
Vaeck et al., "Transgenic Plants Protected from Insect Attack", *Nature* 328:33–37 (Jul. 2, 1987).
Gallo–Meagher et al., "Herbicide Resistant Transgenic Sugarcane Plants Containing the bar Gene", *Crop Sci.*, 36:1367–1374 (1996).
Maier–Greiner et al., "Herbicide Resistance in Transgenic Plants through Degradation of the Phytotoxin in Urea" *Angew. Chem. Int. Ed. Engl.*, vol. 30, No. 10:1314–1315 (1991).

(List continued on next page.)

*Primary Examiner*—David T. Fox
*Assistant Examiner*—Ashwin Mehta
*Attorney, Agent, or Firm*—Alston & Bird LLP

[57] ABSTRACT

The present invention is drawn to compositions and methods for improving transformation efficiency. The compositions, synthetic marker genes, are used in transformation methods and result in increased transformation efficiency. The synthetic marker genes can be designed for maximum expression in any system.

10 Claims, 6 Drawing Sheets

OTHER PUBLICATIONS

D'Halluin et al., "The bar Gene as Selectable and Screenable Marker in Plant Engineering", *Gene,* 103, 171:415–426, Academic Press, (1992).

Rathorn et al., "Use of Bar as a Selectable Marker Gene and for the Production of Herbicide–Resistant Rice Plants from Protoplasts", *Plant Molecular Biology* 2:871–884 (1993).

Tian et al., "High Level of Expression ofModified Green Fluorescent Protein Gene Transfer in Conifer Tissues", In Vitro 32:311 (1996).

Chiu et al. "Engineered GFP as a Vital Reporter in Plants", *Current Biology* 6:325–330 (1996).

Pang et al., "An Improved Green Fluorescent Protein Gene as a Vital Marker in Plants", *Plant Physiology* 112:893–900 (1996).

FIGURE 1

MoPAT Sequence and translation:

```
  1 GGATCCACAC GACACCATGT CCCCCGAGCG CCGCCCCGTC GAGATCCGCC CGGCCACCGC
 61 CGCCGACATG GCCGCCGTGT GCGACATCGT GAACCACTAC ATCGAGACCT CCACCGTGAA
121 CTTCCGCACC GAGCCGCAGA CCCCGCAGGA GTGGATCGAC GACCTGGAGC GCCTCCAGGA
181 CCGCTACCCG TGGCTCGTGG CCGAGGTGGA GGGCGTGGTG GCCGGCATCG CCTACGCCGG
241 CCCGTGGAAG GCCCGCAACG CCTACGACTG GACCGTGGAG TCCACCGTGT ACGTGTCCCA
301 CCGCCACCAG CGCCTCGGCC TCGGCTCCAC CCTCTACACC CACCTCCTCA AGAGCATGGA
361 GGCCCAGGGC TTCAAGTCCG TGGTGGCCGT GATCGGCCTC CCGAACGACC CGTCCGTGCG
421 CCTCCACGAG GCCCTCGGCT ACACCGCCCG CGGCACCCTC CGCGCCGCCG GCTACAAGCA
481 CGGCGGCTGG CACGACGTCG GCTTCTGGCA GCGCGACTTC GAGCTGCCGG CCCCGCCGCG
541 CCCGGTGCGC CCGGTGACGC AGATCTGAGG TGTCGTGTTA AC
```

```
      +1 MetSerProGluArgArgProValGluIleArgProAlaThrAlaAlaAspMetAlaAla
       1 ATGTCCCCCGAGCGCCGCCCCGTCGAGATCCGCCCGGCCACCGCCGCCGACATGGCCGCC
         TACAGGGGGCTCGCGGCGGGGCAGCTCTAGGCGGGCCGGTGGCGGCGGCTGTACCGGCGG

+1 ValCysAspIleValAsnHisTyrIleGluThrSerThrValAsnPheArgThrGluPro
      61 GTGTGCGACATCGTGAACCACTACATCGAGACCTCCACCGTGAACTTCCGCACCGAGCCG
         CACACGCTGTAGCACTTGGTGATGTAGCTCTGGAGGTGGCACTTGAAGGCGTGGCTCGGC

+1 GlnThrProGlnGluTrpIleAspAspLeuGluArgLeuGlnAspArgTyrProTrpLeu
     121 CAGACCCCGCAGGAGTGGATCGACGACCTGGAGCGCCTCCAGGACCGCTACCCGTGGCTC
         GTCTGGGGCGTCCTCACCTAGCTGCTGGACCTCGCGGAGGTCCTGGCGATGGGCACCGAG

+1 ValAlaGluValGluGlyValValAlaGlyIleAlaTyrAlaGlyProTrpLysAlaArg
     181 GTGGCCGAGGTGGAGGGCGTGGTGGCCGGCATCGCCTACGCCGGCCCGTGGAAGGCCCGC
         CACCGGCTCCACCTCCCGCACCACCGGCCGTAGCGGATGCGGCCGGGCACCTTCCGGGCG

+1 AsnAlaTyrAspTrpThrValGluSerThrValTyrValSerHisArgHisGlnArgLeu
     241 AACGCCTACGACTGGACCGTGGAGTCCACCGTGTACGTGTCCCACCGCCACCAGCGCCTC
         TTGCGGATGCTGACCTGGCACCTCAGGTGGCACATGCACAGGGTGGCGGTGGTCGCGGAG

+1 GlyLeuGlySerThrLeuTyrThrHisLeuLeuLysSerMetGluAlaGlnGlyPheLys
     301 GGCCTCGGCTCCACCCTCTACACCCACCTCCTCAAGAGCATGGAGGCCCAGGGCTTCAAG
```

FIGURE 1 (cont.)

```
          CCGGAGCCGAGGTGGGAGATGTGGGTGGAGGAGTTCTCGTACCTCCGGGTCCCGAAGTTC

+1 SerValValAlaValIleGlyLeuProAsnAspProSerValArgLeuHisGluAlaLeu
     361 TCCGTGGTGGCCGTGATCGGCCTCCCGAACGACCCGTCCGTGCGCCTCCACGAGGCCCTC
         AGGCACCACCGGCACTAGCCGGAGGGCTTGCTGGGCAGGCACGCGGAGGTGCTCCGGGAG

+1 GlyTyrThrAlaArgGlyThrLeuArgAlaAlaGlyTyrLysHisGlyGlyTrpHisAsp
     421 GGCTACACCGCCCGCGGCACCCTCCGCGCCGCCGGCTACAAGCACGGCGGCTGGCACGAC
         CCGATGTGGCGGGCGCCGTGGGAGGCGCGGCGGCCGATGTTCGTGCCGCCGACCGTGCTG

+1 ValGlyPheTrpGlnArgAspPheGluLeuProAlaProProArgProValArgProVal
     481 GTCGGCTTCTGGCAGCGCGACTTCGAGCTGCCGGCCCCGCCGCGCCCGGTGCGCCCGGTG
         CAGCCGAAGACCGTCGCGCTGAAGCTCGACGGCCGGGGCGGCGCGGGCCACGCGGGCCAC

+1 ThrGlnIle***
     541 ACGCAGATCTGA
         TGCGTCTAGACT
```

FIGURE 2

```
  1  TCGCGCGTTT  CGGTGATGAC  GGTGAAAACC  TCTGACACAT  GCAGCTCCCG
     AGCGCGCAAA  GCCACTACTG  CCACTTTTGG  AGACTGTGTA  CGTCGAGGGC

51  GAGACGGTCA  CAGCTTGTCT  GTAAGCGGAT  GCCGGGAGCA  GACAAGCCCG
     CTCTGCCAGT  GTCGAACAGA  CATTCGCCTA  CGGCCCTCGT  CTGTTCGGGC

101  TCAGGGCGCG  TCAGCGGGTG  TTGGCGGGTG  TCGGGGCTGG  CTTAACTATG
     AGTCCCGCGC  AGTCGCCCAC  AACCGCCCAC  AGCCCCGACC  GAATTGATAC

151  CGGCATCAGA  GCAGATTGTA  CTGAGAGTGC  ACCATATGCG  GTGTGAAATA
     GCCGTAGTCT  CGTCTAACAT  GACTCTCACG  TGGTATACGC  CACACTTTAT

201  CCGCACAGAT  GCGTAAGGAG  AAAATACCGC  ATCAGGCGCC  ATTCGCCATT
     GGCGTGTCTA  CGCATTCCTC  TTTTATGGCG  TAGTCCGCGG  TAAGCGGTAA

251  CAGGCTGCGC  AACTGTTGGG  AAGGGCGATC  GGTGCGGGCC  TCTTCGCTAT
     GTCCGACGCG  TTGACAACCC  TTCCCGCTAG  CCACGCCCGG  AGAAGCGATA

301  TACGCCAGCT  GGCGAAAGGG  GGATGTGCTG  CAAGGCGATT  AAGTTGGGTA
     ATGCGGTCGA  CCGCTTTCCC  CCTACACGAC  GTTCCGCTAA  TTCAACCCAT
                                                    HindIII
351  ACGCCAGGGT  TTTCCCAGTC  ACGACGTTGT  AAAACGACGG  CCAGTGCCAA
     TGCGGTCCCA  AAAGGGTCAG  TGCTGCAACA  TTTTGCTGCC  GGTCACGGTT
     HindIII                            HpaI
401  GCTTGCATGC  CTGCAGGTCG  ACTCTAGAGT  TAACACGACA  CCTCACTCCC
     CGAACGTACG  GACGTCCAGC  TGAGATCTCA  ATTGTGCTGT  GGAGTGAGGG 451  ACGGCTTCAT  CAGGGTGTTG  GCCTCCATCT  GCTTGTCGAA  CTGCGGGATG
     TGCCGAAGTA  GTCCCACAAC  CGGAGGTAGA  CGAACAGCTT  GACGCCCTAC 501  TGGGTGGTGT  GGCACCACGG  CTTGTTGGAC  TCCTCCTTGC  GCACGGTGCA
     ACCCACCACA  CCGTGGTGCC  GAACAACCTG  AGGAGGAACG  CGTGCCACGT 551  GGCGAACCAG  GAGCACCAGC  CGTGGCGCGG  GAAGGCGGTG  TTGATGGAGT
     CCGCTTGGTC  CTCGTGGTCG  GCACCGCGCC  CTTCCGCCAC  AACTACCTCA 601  TGCGGGTGGT  GTCGTCCACC  CAGGAGCCGA  AGTCGTCGAT  GCCGTCGTAG
     ACGCCCACCA  CAGCAGGTGG  GTCCTCGGCT  TCAGCAGCTA  CGGCAGCATC 651  GCGCCCACGT  TGTCGTAGAG  GGTGGCGAGC  TGGATGAGCT  GGCCGAGGAA
     CGCGGGTGCA  ACAGCATCTC  CCACCGCTCG  ACCTACTCGA  CCGGCTCCTT 701  GGTGATGTTG  CCGTCGACGC  CGACGTCCTC  GTGGCGGATG  ATGGCCTCGG
     CCACTACAAC  GGCAGCTGCG  GCTGCAGGAG  CACCGCCTAC  TACCGGAGCC 751  CCACCGCCTC  CGCCTGGTCG  GTGGAGGAGC  CGAGCACCT   GAGGACCTCC
     GGTGGCGGAG  GCGGACCAGC  CACCTCCTCG  GCTCGTGGAA  CTCCTGGAGG 801  ATCGCCTTGA  TGCCGCCGTA  GATGTCGAAG  GACATGCGGG  TGGAGGTGAA
     TAGCGGAACT  ACGGCGGCAT  CTACAGCTTC  CTGTACGCCC  ACCTCCACTT 851  GTAGGCCTCG  GCGGTGCCCA  CGTCGTGGAG  GAGGCAGGTG  AGGGCCCAGG
     CATCCGGAGC  CGCCACGGGT  GCAGCACCTC  CTCCGTCCAC  TCCCGGGTCC
```

FIGURE 2 (cont.)

```
 901  TGGACGGGGA GAGGTCCTTG GCCTGCTCCG GGAGGAGCCT CCTGGCGATC
      ACCTGCCCCT CTCCAGGAAC CGGACGAGGC CCTCCTCGGA GGACCGCTAG

951  ACGGTGCCCC AGTAGAACAC GCGCATGGAG TGGTTGTAGG TCTCCGGGGA
      TGCCACGGGG TCATCTTGTG CGCGTACCTC ACCAACATCC AGAGGCCCCT

1001  GAGGCGGGCC TTGACGAACG CCTGGGCCTC GGCCACGAGC TTGTCGGCCG
      CTCCGCCCGG AACTGCTTGC GGACCCGGAG CCGGTGCTCG AACAGCCGGC

1051  CTGGGAAGGC GATGTCCTCC ACGGAGTAGG AGCTGACGTC GCCGAGCTTG
      GACCCTTCCG CTACAGGAGG TGCCTCATCC TCGACTGCAG CGGCTCGAAC

1101  CCGAGGGAGT CCACGATGGC CTTGGCGCTG ACGGGGACCG CGGTCCAGCC
      GGCTCCCTCA GGTGCTACCG GAACCGCGAC TGCCCCTGGC GCCAGGTCGG
                                                  BamHI
1151  GTTGGCCTTC ACCTCGGAGG ACGACATGGT GTCGTGTGGA TCCCCGGGTA
      CAACCGGAAG TGGAGCCTCC TGCTGTACCA CAGCACACCT AGGGGCCCAT
      EcoRI
1201  CCGAATTCGT AATCATGGTC ATAGCTGTTT CCTGTGTGAA ATTGTTATCC
      GGCTTAAGCA TTAGTACCAG TATCGACAAA GGACACACTT TAACAATAGG

1251  GCTCACAATT CCACACAACA TACGAGCCGG AAGCATAAAG TGTAAAGCCT
      CGAGTGTTAA GGTGTGTTGT ATGCTCGGCC TTCGTATTTC ACATTTCGGA

1301  GGGGTGCCTA ATGAGTGAGC TAACTCACAT TAATTGCGTT GCGCTCACTG
      CCCCACGGAT TAGTCACTCG ATTGAGTGTA ATTAACGCAA CGCGAGTGAC

1351  CCCGCTTTCC AGTCGGGAAA CCTGTCGTGC CAGCTGCATT AATGAATCGG
      GGGCGAAAGG TCAGCCCTTT GGACAGCACG GTCGACGTAA TTACTTAGCC

1401  CCAACGCGCG GGGAGAGGCG GTTTGCGTAT TGGGCGCTCT TCCGCTTCCT
      GGTTGCGCGC CCCTCTCCGC CAAACGCATA ACCCGCGAGA AGGCGAAGGA

1451  CGCTCACTGA CTCGCTGCGC TCGGTCGTTC GGCTGCGGCG AGCGGTATCA
      GCGAGTGACT GAGCGACGCG AGCCAGCAAG CCGACGCCGC TCGCCATAGT

1501  GCTCACTCAA AGGCGGTAAT ACGGTTATCC ACAGAATCAG GGGATAACGC
      CGAGTGAGTT TCCGCCATTA TGCCAATAGG TGTCTTAGTC CCCTATTGCG

1551  AGGAAAGAAC ATGTGAGCAA AAGGCCAGCA AAAGGCCAGG AACCGTAAAA
      TCCTTTCTTG TACACTCGTT TTCCGGTCGT TTTCCGGTCC TTGGCATTTT

1601  AGGCCGCGTT GCTGGCGTTT TTCCATAGGC TCCGCCCCCC TGACGAGCAT
      TCCGGCGCAA CGACCGCAAA AAGGTATCCG AGGCGGGGGG ACTGCTCGTA

1651  CACAAAAATC GACGCTCAAG TCAGAGGTGG CGAAACCCGA CAGGACTATA
      GTGTTTTTAG CTGCGAGTTC AGTCTCCACC GCTTTGGGCT GTCCTGATAT

1701  AAGATACCAG GCGTTTCCCC CTGGAAGCTC CCTCGTGCGC TCTCCTGTTC
      TTCTATGGTC CGCAAAGGGG GACCTTCGAG GGAGCACGCG AGAGGACAAG

1751  CGACCCTGCC GCTTACCGGA TACCTGTCCG CCTTTCTCCC TTCGGGAAGC
      GCTGGGACGG CGAATGGCCT ATGGACAGGC GGAAAGAGGG AAGCCCTTCG
```

FIGURE 2 (cont.)

```
1801  GTGGCGCTTT CTCATAGCTC ACGCTGTAGG TATCTCAGTT CGGTGTAGGT
      CACCGCGAAA GAGTATCGAG TGCGACATCC ATAGAGTCAA GCCACATCCA

1851  CGTTCGCTCC AAGCTGGGCT GTGTGCACGA ACCCCCCGTT CAGCCCGACC
      GCAAGCGAGG TTCGACCCGA CACACGTGCT TGGGGGGCAA GTCGGGCTGG

1901  GCTGCGCCTT ATCCGGTAAC TATCGTCTTG AGTCCAACCC GGTAAGACAC
      CGACGCGGAA TAGGCCATTG ATAGCAGAAC TCAGGTTGGG CCATTCTGTG
                           AlwNI
1951  GACTTATCGC CACTGGCAGC AGCCACTGGT AACAGGATTA GCAGAGCGAG
      CTGAATAGCG GTGACCGTCG TCGGTGACCA TTGTCCTAAT CGTCTCGCTC

2001  GTATGTAGGC GGTGCTACAG AGTTCTTGAA GTGGTGGCCT AACTACGGCT
      CATACATCCG CCACGATGTC TCAAGAACTT CACCACCGGA TTGATGCCGA

2051  ACACTAGAAG GACAGTATTT GGTATCTGCG CTCTGCTGAA GCCAGTTACC
      TGTGATCTTC CTGTCATAAA CCATAGACGC GAGACGACTT CGGTCAATGG

2101  TTCGGAAAAA GAGTTGGTAG CTCTTGATCC GGCAAACAAA CCACCGCTGG
      AAGCCTTTTT CTCAACCATC GAGAACTAGG CCGTTTGTTT GGTGGCGACC

2151  TAGCGGTGGT TTTTTTGTTT GCAAGCAGCA GATTACGCGC AGAAAAAAAG
      ATCGCCACCA AAAAAACAAA CGTTCGTCGT CTAATGCGCG TCTTTTTTTC

2201  GATCTCAAGA AGATCCTTTG ATCTTTTCTA CGGGGTCTGA CGCTCAGTGG
      CTAGAGTTCT TCTAGGAAAC TAGAAAAGAT GCCCCAGACT GCGAGTCACC

2251  AACGAAAACT CACGTTAAGG GATTTTGGTC ATGAGATTAT CAAAAAGGAT
      TTGCTTTTGA GTGCAATTCC CTAAAACCAG TACTCTAATA GTTTTTCCTA

2301  CTTCACCTAG ATCCTTTTAA ATTAAAAATG AAGTTTTAAA TCAATCTAAA
      GAAGTGGATC TAGGAAAATT TAATTTTTAC TTCAAAATT  AGTTAGATTT

2351  GTATATATGA GTAAACTTGG TCTGACAGTT ACCAATGCTT AATCAGTGAG
      CATATATACT CATTTGAACC AGACTGTCAA TGGTTACGAA TTAGTCACTC

2401  GCACCTATCT CAGCGATCTG TCTATTTCGT TCATCCATAG TTGCCTGACT
      CGTGGATAGA GTCGCTAGAC AGATAAAGCA AGTAGGTATC AACGGACTGA

2451  CCCCGTCGTG TAGATAACTA CGATACCGGA GGGCTTACCA TCTGGCCCCA
      GGGGCAGCAC ATCTATTGAT GCTATGGCCT CCCGAATGGT AGACCGGGGT

2501  GTGCTGCAAT GATACCGCGA GACCCACGCT CACCGGCTCC AGATTTATCA
      CACGACGTTA CTATGGCGCT CTGGGTGCGA GTGGCCGAGG TCTAAATAGT

2551  GCAATAAACC AGCCAGCCGG AAGGGCCGAG CGCAGAAGTG GTCCTGCAAC
      CGTTATTTGG TCGGTCGGCC TTCCCGGCTC GCGTCTTCAC CAGGACGTTG

2601  TTTATCCGCC TCCATCCAGT CTATTAATTG TTGCCGGGAA GCTAGAGTAA
      AAATAGGCGG AGGTAGGTCA GATAATTAAC AACGGCCCTT CGATCTCATT

2651  GTAGTTCGCC AGTTAATAGT TTGCGCAACG TTGTTGCCAT TGCTACAGGC
      CATCAAGCGG TCAATTATCA AACGCGTTGC AACAACGGTA ACGATGTCCG
```

FIGURE 2 (cont.)

```
2701 ATCGTGGTGT CACGCTCGTC GTTTGGTATG GCTTCATTCA GCTCCGGTTC
     TAGCACCACA GTGCGAGCAG CAAACCATAC CGAAGTAAGT CGAGGCCAAG

2751 CCAACGATCA AGGCGAGTTA CATGATCCCC CATGTTGTGC AAAAAAGCGG
     GGTTGCTAGT TCCGCTCAAT GTACTAGGGG GTACAACACG TTTTTTCGCC

2801 TTAGCTCCTT CGGTCCTCCG ATCGTTGTCA GAAGTAAGTT GGCCGCAGTG
     AATCGAGGAA GCCAGGAGGC TAGCAACAGT CTTCATTCAA CCGGCGTCAC

2851 TTATCACTCA TGGTTATGGC AGCACTGCAT AATTCTCTTA CTGTCATGCC
     AATAGTGAGT ACCAATACCG TCGTGACGTA TTAAGAGAAT GACAGTACGG

2901 ATCCGTAAGA TGCTTTTCTG TGACTGGTGA GTACTCAACC AAGTCATTCT
     TAGGCATTCT ACGAAAAGAC ACTGACCACT CATGAGTTGG TTCAGTAAGA

2951 GAGAATAGTG TATGCGGCCA CCGAGTTGCT CTTGCCCGGC GTCAATACGG
     CTCTTATCAC ATACGCCGT GGCTCAACGA GAACGGGCCG CAGTTATGCC
                                                   Asp700
3001 GATAATACCG CGCCACATAG CAGAACTTTA AAAGTGCTCA TCATTGGAAA
     CTATTATGGC GCGGTGTATC GTCTTGAAAT TTTCACGAGT AGTAACCTTT
     Asp700
3051 ACGTTCTTCG GGGCGAAAAC TCTCAAGGAT CTTACCGCTG TTGAGATCCA
     TGCAAGAAGC CCCGCTTTTG AGAGTTCCTA GAATGGCGAC AACTCTAGGT

3101 GTTCGATGTA ACCCACTCGT GCACCCAACT GATCTTCAGC ATCTTTTACT
     CAAGCTACAT TGGGTGAGCA CGTGGGTTGA CTAGAAGTCG TAGAAAATGA

3151 TTCACCAGCG TTTCTGGGTG AGCAAAAACA GGAAGGCAAA ATGCCGCAAA
     AAGTGGTCGC AAAGACCCAC TCGTTTTTGT CCTTCCGTTT TACGGCGTTT

3201 AAAGGGAATA AGGGCGACAC GGAAATGTTG AATACTCATA CTCTTCCTTT
     TTTCCCTTAT TCCCGCTGTG CCTTTACAAC TTATGAGTAT GAGAAGGAAA

3251 TTCAATATTA TTGAAGCATT TATCAGGGTT ATTGTCTCAT GAGCGGATAC
     AAGTTATAAT AACTTCGTAA ATAGTCCCAA TAACAGAGTA CTCGCCTATG

3301 ATATTTGAAT GTATTTAGAA AAATAAACAA ATAGGGGTTC CGCGCACATT
     TATAAACTTA CATAAATCTT TTTATTTGTT TATCCCCAAG GCGCGTGTAA

3351 TCCCCGAAAA GTGCCACCTG ACGTCTAAGA AACCATTATT ATCATGACAT
     AGGGGCTTTT CACGGTGGAC TGCAGATTCT TTGGTAATAA TAGTACTGTA

3401 TAACCTATAA AAATAGGCGT ATCACGAGGC CCTTTCGTC
     ATTGGATATT TTTATCCGCA TAGTGCTCCG GGAAAGCAG
```

METHODS FOR IMPROVING TRANSFORMATION EFFICIENCY

CROSS-REFERENCE TO RELATED APPLICATIONS

This application is a Continuation-In-Part of Provisional application Ser. No. 60/035,560 filed Jan. 14, 1997.

FIELD OF THE INVENTION

The invention relates to the genetic modification of organisms, particularly plants.

BACKGROUND OF THE INVENTION

Gene transfer has offered great promise in the genetic manipulation of organisms. The movement of genes within plant species has played an important role in crop improvement for many decades. The recombinant DNA methods which have been developed have greatly extended the sources from which genetic information can be obtained for crop improvement. Gene transfer systems based on recombinant DNA are available for several crop species and are under development for many others.

Rapid progress has been made in developing the tools for manipulating genetic information in plants. Plant genes are being cloned, genetic regulatory signals deciphered, and genes transferred from entirely unrelated organisms to confer new agriculturally useful traits to crop plants. Recombinant DNA methods significantly increase the gene pool available for crop improvement.

A variety of methods have been developed for the transformation of plants and plant cells with DNA. Generally, the most success has been in dicotyledonous plants. Some success has been reported with certain monocotyledonous cereals.

Cereals comprise a commercially valuable group of plant species that could benefit from the introduction and expression of foreign genes controlling improved grain quality and such agronomically important traits as tolerance to disease, insects, herbicides, and stress. However, most cereals have not proven readily amenable to either Agrobacterium-mediated gene delivery, or to the routine regeneration of fertile transgenic plants from directly transformed protoplasts. The use of microprojectile-bombardment-mediated transformation of embryogenic tissue culture material, with the subsequent regeneration of transgenic plants, has overcome the regeneration problems associated with the production of plants from cereal protoplasts. Using this technology, transgenic plants have been obtained from microprojectile-bombarded tissue cultures of many species.

Many of the recent advances in plant science have resulted from application of the analytical power of recombinant DNA technology coupled with plant transformation. These approaches facilitate studies of the effects of specific gene alterations and additions on plant development and physiology. They also make possible the direct manipulation of genes to bio-engineer improved plant varieties.

While strides have been made in the genetic transformation of plants, it is by no means a routine matter. In fact, transformation efficiency is quite low making the process very labor intensive. Some reports indicate that the current transformation methods provide only a transformation frequency of about one event from every thousand bombarded embryos. This transformation frequency is too low for many genetic studies and for routine commerical applications. Therefore, a method is needed to improve the efficiency of genetic transformation.

SUMMARY OF THE INVENTION

Compositions and methods for improving transformation efficiency in organisms, particularly plants, are provided. The compositions, synthetic marker genes, are used in transformation methods and result in increased transformation efficiency. The synthetic marker genes can be designed for maximum expression in any system.

DESCRIPTION OF THE FIGURES

FIG. 1: Nucleotide sequence of phosphinothricin acetyltransferase optimized for expression in monocots (SEQ ID NO:3).

FIG. 2: Nucleotide sequence of cyanamide hydratase optimized for expression in monocots (SEQ ID NO:7).

DETAILED DESCRIPTION OF THE INVENTION

The present invention is drawn to compositions and methods for improving transformation efficiency in organisms, particularly plants. For use in plants, the method involves stably transforming a plant cell or culture and regenerating plants from the transformed cells. Using the methods of the invention, fertile transgenic plants can be grown to maturity with a high frequency. The fertile transformed plants are capable of producing transformed progeny that express foreign genes of interest.

The methods of the present invention improve transformation efficiency. By improve efficiency it is intended that the number of transformed plants recovered by a transformation attempt is increased preferably at least two fold, preferably at least five fold, more preferably at least ten fold.

The present invention thus encompasses the fertile transgenic plants and transformed seeds thereof, as well as the subsequent progeny and products derived therefrom.

By transformation is intended the genetic manipulation of the plant, cell, cell line, callus, tissue, plant part, and the like. That is, such cell, cell line, callus, tissue, plant part, or plant which has been altered by the presence of recombinant DNA wherein said DNA is introduced into the genetic material within the cell, either chromosomally, or extra-chromosomally. Recombinant DNA includes foreign DNA, heterologous DNA, exogenous DNA, and chimeric DNA.

The transformed plants of the invention can be produced by genetic engineering. Alternatively, transformed parent plants can be produced by genetic engineering and used to transfer the foreign genes into subsequent generations by sexual or asexual reproduction.

The methods of the present invention can be used in combination with any means for transformation of plants or plant cells. The present invention provides for the use of an optimized marker gene. The marker gene can be optimized for expression in a particular plant species, a particular genus of plants or a particular group of plants, for example monocots and/or dicots, maize, wheat, soybean, and the like.

By marker gene is intended both selectable marker genes and reporter genes. Both selectable marker genes and reporter genes facilitate identification and selection of transformed cells. To date, all genetic transformation systems which have been developed rely upon a selectable marker or reporter gene to enable the recovery of transgenic plants.

Reporter genes should ideally exhibit low background activity and should not have any detrimental effects on metabolism. The reporter gene products will have moderate stability in vivo, so that down-regulation of gene expression as well as gene activity can be detected. Finally, the reporter gene should be able to be assayed by a non-destructive, quantitative, sensitive, simple to perform and inexpensive system.

Reporter genes are known in the art and include but are not limited to:

Beta-glucuronidase (GUS) gene (Jefferson et al. (1991) *In Plant Molecular Biology Manual* (Gelvin et al., eds.), pp. 1–33, Kluwer Academic Publishers). This gene is encoded by the uidA locus of *E. coli*. GUS enzyme activity can be assayed easily and sensitively in plants. The expression of GUS gene fusions can be quantified by fluorometric assay, and histochemical analysis can be used to localize gene activity in transgenic tissues.

Luciferase (DeWet et al. (1987) *Mol. Cell. Biol.*, 7:725–737). Luciferase catalyzes the oxidation of D(−)-luciferin in the presence of ATP to generate oxyluciferin and yellow-green light.

Anthocyanins (Goff et al. (1990) *EMBO J.*, 9:2517–2522). Anthocyanin is a reporter system that does not require the application of external substrates for its detection. The anthocyanin system utilizes the C1, B and R genes, which code for trans-acting factors that regulate the anthocyanin biosynthetic pathway in maize seeds. The introduction of these regulatory genes under the control of constitutive promoters includes cell-autonomous pigmentation in non-seed tissues.

Green fluorescent protein (GFP) from the jellyfish *Aequorea victoria* (Kain et al. (1995) *BioTechniques*, 19:650–655 and Chiu et al. (1996) *Current Biology*, 6:325–330). GFP emits bright green light when excited with UV or blue light. GFP fluorescence does not require a substrate or cofactor, is stable, and can be monitored non-invasively in living cells.

Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. (See DeBlock et al. (1987) *EMBO J.*, 6:2513–2518; DeBlock et al. (1989) *Plant Physiol.*, 91:691–704; Fromm et al. (1990) 8:833–839; Gordon-Kamm et al. (1990) 2:603–618) For example, resistance to glyphosate or sulfonylurea herbicides has been obtained by using genes coding for the mutant target enzymes, 5-enolpyruvylshikimate-3-phosphate synthase (EPSPS) and acetolactate synthase (ALS). Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to genes encoding: neomycin phosphotransferase II (Fraley et al. (1986) *CRC Critical Reviews in Plant Science*, 4:1–25); cyanamide hydratase (Maier-Greiner et al. (1991) *Proc. Natl. Acad. Sci. USA*, 88:4250–4264); aspartate kinase; dihydrodipicolinate synthase (Perl et al. (1993) *Bio/Technology*, 11:715–718); tryptophan decarboxylase (Goddijn et al. (1993) *Plant Mol. Bio.*, 22:907–912); dihydrodipicolinate synthase and desensitized aspartade kinase (Perl et al. (1993) *Bio/Technology*, 11:715–718); bar gene (Toki et al. (1992) *Plant Physiol.*, 100:1503–1507 and Meagher et al. (1996) and *Crop Sci.*, 36:1367); tryptophan decarboxylase (Goddijn et al. (1993) *Plant Mol. Biol.*, 22:907–912); neomycin phosphotransferase (NEO) (Southern et al. (1982) *J. Mol. Appl. Gen.*, 1:327; hygromycin phosphotransferase (HPT or HYG) (Shimizu et al. (1986) *Mol. Cell Biol.*, 6:1074); dihydrofolate reductase (DHFR) (Kwok et al. (1986) *PNAS USA* 4552); phosphinothricin acetyltransferase (DeBlock et al. (1987) *EMBO J.*, 6:2513); 2,2-dichloropropionic acid dehalogenase (Buchanan-Wollatron et al. (1989) *J. Cell. Biochem.* 13D:330); acetohydroxyacid synthase (Anderson et al., U.S. Pat. No. 4,761,373; Haughn et al. (1988) *Mol. Gen. Genet.* 221:266); 5-enolpyruvyl-shikimate-phosphate synthase (aroA) (Comai et al. (1985) *Nature* 317:741); haloarylnitrilase (Stalker et al., published PCT applcn WO87/04181); acetyl-coenzyme A carboxylase (Parker et al. (1990) *Plant Physiol.* 92:1220); dihydropteroate synthase (sul I) (Guerineau et al. (1990) *Plant Mol. Biol.* 15:127); 32 kD photosystem II polypeptide (psbA) (Hirschberg et al. (1983) *Science*, 222:1346); etc.

Also included are genes encoding resistance to: chloramphenicol (Herrera-Estrella et al. (1983) *EMBO J.*, 2:987–992); methotrexate (Herrera-Estrella et al. (1983) *Nature*, 303:209–213; Meijer et al. (1991) *Plant Mol Bio.*, 16:807–820 (1991); hygromycin (Waldron et al. (1985) *Plant Mol. Biol.*, 5:103–108; Zhijian et al. (1995) *Plant Science*, 108:219–227 and Meijer et al. (1991) *Plant Mol. Bio.* 16:807–820); streptomycin (Jones et al. (1987) *Mol. Gen. Genet.*, 210:86–91); spectinomycin (Bretagne-Sagnard et al. (1996) *Transgenic Res.*, 5:131–137); bleomycin (Hille et al. (1986) *Plant Mol. Biol.*, 7:171–176); sulfonamide (Guerineau et al. (1990) *Plant Mol. Bio.*, 15:127–136); bromoxynil (Stalker et al. (1988) *Science*, 242:419–423); 2,4-D (Streber et al. (1989) *Bio/Technology*, 7:811–816); glyphosate (Shaw et al. (1986) *Science*, 233:478–481); phosphinothricin (DeBlock et al. (1987) *EMBO J.*, 6:2513–2518).

See generally, G. T. Yarranton (1992) *Curr. Opin. Biotech.*, 3:506–511; Christopherson et al. (1992) *Proc. Natl. Acal. Sci. USA*, 89:6314–6318; Yao et al. (1992) *Cell*, 71:63–72; W. S. Reznikoff (1992) *Mol. Microbiol.*, 6:2419–2422; Barkley et al. (1980) *The Operon*, pp. 177–220; Hu et al. (1987) *Cell*, 48:555–566; Brown et al. (1987) *Cell*, 49:603–612; Figge et al. (1988) *Cell*, 52:713–722; Deuschle et al. (1989) *Proc. Natl. Acad. Aci. USA*, 86:5400–5404; Fuerst et al. (1989) *Proc. Natl. Acad. Sci. USA*, 86:2549–2553; Deuschle et al. (1990) *Science*, 248:480–483; M. Gossen (1993) PhD Thesis, University of Heidelberg; Reines et al. (1993) *Proc. Natl. Acad. Sci. USA*, 90:1917–1921; Labow et al. (1990) *Mol. Cell Bio.*, 10:3343–3356; Zambretti et al. (1992) *Proc. Natl. Acad. Sci. USA*, 89:3952–3956; Baim et al. (1991) *Proc. Natl. Acad. Sci. USA*, 88:5072–5076; Wyborski et al. (1991) *Nuc. Acids Res.*, 19:4647–4653; A. Hillenand-Wissman (1989) *Topics in Mol. and Struc. Biol.*, 10:143–162; Degenkolb et al. (1991) *Antimicrob. Agents Chemother.*, 35:1591–1595; Kleinschnidt et al. (1988) *Biochemistry*, 27:1094–1104; Gatz et al. (1992) *Plant J.*, 2:397–404; A. L. Bonin (1993) PhD Thesis, University of Heidelberg; Gossen et al. (1992) *Proc. Natl. Acad. Sci. USA*, 89:5547–5551; Oliva et al. (1992) *Antimicrob. Agents Chemother.*, 36:913–919; Hlavka et al. (1985) *Handbook of Exp. Pharmacology*, 78; Gill et al. (1988) *Nature* 334:721–724. Such disclosures are herein incorporated by reference.

The above list of selectable marker and reporter genes are not meant to be limiting. Any reporter or selectable marker gene are encompassed by the present invention. If necessary, such genes can be sequenced by methods known in the art.

The reporter and selectable marker genes are synthesized for optimal expression in the plant. That is, the coding sequence of the gene has been modified to enhance expression in plants. The synthetic marker gene is designed to be expressed in plants at a higher level resulting in higher transformation efficiency.

Methods for synthetic optimization of genes are available in the art. In fact, several genes have been optimized to increase expression of the gene product in plants. However, until the present invention no one had recognized that transformation efficiency could be improved by genetic modification of the marker gene for optimal expression in the cell being transformed.

The marker gene sequence can be optimized for expression in a particular plant species or alternatively can be modified for optimal expression in plant families. The plant preferred codons may be determined from the codons of highest frequency in the proteins expressed in the largest amount in the particular plant species of interest. See, for example, EPA 0359472; EPA 0385962; WO 91/16432; Perlak et al. (1991) Proc. Natl. Acad. Sci. USA, 88:3324–3328; and Murray et al. (1989) Nucleic Acids Research, 17: 477498. U.S. Pat. No. 5,380,831; U.S. Pat. No. 5,436,391; and the like, herein incorporated by reference. In this manner, the nucleotide sequences can be optimized for expression in any plant. It is recognized that all or any part of the gene sequence may be optimized or synthetic. That is, fully optimized or partially optimized sequences may also be used.

In the same manner, genes can be optimized for expression in any organism. Thus, while the invention is described in relation to improving the transformation efficiency in plants, the methods of the invention can be applied to improving the transformation efficiency in any system.

The marker genes of the invention are provided in expression cassettes for expression in the organism of interest. In this manner, the cassette will include 5' and 3' regulatory sequences operably linked to the gene of interest. Additionally, the expression cassette may be linked at the 5' end to various promoters from the same or different organisms. These promoters would be selected for strength and/or inducibility. Examples of such promoters include but are not limited to the ubiquitin-1 (Ubi-1) promoter or the cauliflower mosaic virus 35S (CaMv) promoter. See for example Christensen et al. (1992) Plant Mol. Biol. 18:675–689; Cornijo et al. (1993) Plant Mol. Biol. 23:567–581; Hohn et al. (1993) PNAS 93(16):8334–8339. The expression cassette may also include 3' terminator regions linked to the gene of interest examples of which are the CaMV 35S terminator and the potato proteinase inhibitor protein or pin II terminator. See for example, Mitsuhara et al. (1996) Plant Cell Physiol. 37(1):49–59; Seymour et al. (1993) Plant Mol. Biol. 23(1): 1–9; The cassette may additionally contain at least one gene to be cotransformed into the organism. Alternatively, the additional gene(s) of interest can be provided on another expression cassette. Where appropriate, the additional gene(s) of interest may be optimized for increased expression in the transformed plant.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) PNAS USA, 86:6126–6130); potyvirus leaders, for example, TEV leader (Tobacco Etch Virus) (Allison et al. (1986); MDMV leader (Maize Dwarf Mosaic Virus); Virology, 154:9–20), and human immunoglobulin heavy-chain binding protein (BiP), (Macejak, D. G., and P. Sarnow (1991) Nature, 353:90–94; untranslated leader from the coat protein mRNA of alfalfa mosaic virus (AMV RNA 4), (Jobling, S. A., and Gehrke, L., (1987) Nature, 325:622–625; tobacco mosaic virus leader (TMV), (Gallie, D. R. et al. (1989) Molecular Biology of RNA, pages 237–256; and maize chlorotic mottle virus leader (MCMV) (Lommel, S. A. et al. (1991) Virology, 81:382–385). See also, Della-Cioppa et al. (1987) Plant Physiology, 84:965–968. Other methods known to enhance translation can also be utilized, for example, introns, and the like.

In preparing the expression cassette, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The compositions and methods of the present invention can be used in any transformation protocol. Such transformation protocols may vary depending on the type of plant or plant cell, i.e. monocot or dicot, targeted for transformation. Suitable methods of transforming plant cells include microinjection (Crossway et al. (1986) Biotechniques 4:320–334), electroporation (Riggs et al. (1986) Proc. Natl. Acad. Sci. USA, 83:5602–5606, Agrobacterium mediated transformation (Hinchee et al. (1988) Biotechnology, 6:915–921), direct gene transfer (Paszkowski et al. (1984) EMBO J., 3:2717–2722), and ballistic particle acceleration (see, for example, Sanford et al., U.S. Pat. No. 4,945,050; WO91/10725 and McCabe et al. (1988) Biotechnology, 6:923–926). Also see, Weissinger et al. (1988) Annual Rev. Genet., 22:421–477; Sanford et al. (1987) Particulate Science and Technology, 5:27–37 (onion); Christou et al. (1988) Plant Physiol. 87:671–674 (soybean); McCabe et al. (1988) Bio/Technology, 6:923–926 (soybean); Datta et al. (1990) Biotechnology, 8:736–740(rice); Klein et al. (1988) Proc. Natl. Acad. Sci. USA, 85:4305–4309 (maize); Klein et al. (1988) Biotechnology, 6:559–563 (maize); WO91/10725 (maize); Klein et al. (1988) Plant Physiol., 91:440–444 (maize); Fromm et al. (1990) Biotechnology, 8:833–839; and Gordon-Kamm et al. (1990) Plant Cell, 2:603–618 (maize); Hooydaas-Van Slogteren & Hooykaas (1984) Nature (London), 311:763–764; Bytebier et al. (1987) Proc. Natl. Acad. Sci. USA, 84:5345–5349 (Liliaceae); De Wet et al. (1985) In The Experimental Manipulation of Ovule Tissues, ed. G. P. Chapman et al., pp. 197–209. Longman, N.Y. (pollen); Kaeppler et al. (1990) Plant Cell Reports, 9:415–418; and Kaeppler et al. (1992) Theor. Appl. Genet., 84:560–566 (whisker-mediated transformation); D'Halluin et al. (1992) Plant Cell, 4:1495–1505 (electroporation); Li et al. (1993) Plant Cell Reports, 12:250–255 and Christou and Ford (1995) Annals of Botany, 75:407–413 (rice); Osjoda et al. (1996) Nature Biotechnology, 14:745–750 (maize via Agrobacterium tumefaciens); all of which are herein incorporated by reference.

The plant plastid can also be transformed directly. Stable transformation of plastids have been reported in higher plants. See, for example, Svab et al. (1990) Proc. Nat'l. Acad. Sci. USA, 87:8526–8530; Svab & Maliga (1993) Proc.

Nat'l Acad. Sci. USA, 90:913–917; Svab & Maliga (1993) EMBO J., 12:601–606. The method relies on particular gun delivery of DNA containing a selectable marker and targeting of the DNA to the plastid genome through homologous recombination. Additionally, plastid transformation can be accomplished by trans-activation of a silent plastid-borne transgene by tissue-specific expression of a nuclear-encoded and plastid-directed RNA polymerase. Such a system has been reported in McBride et al. (1994) Proc. Natl. Acad. Sci., USA, 91:7301–7305. Where the transformation protocol is directed to plastid transformation, the marker genes are optimized for expression in the plant plastid.

The cells which have been transformed may be grown into plants in accordance with conventional ways. See, for example, McCormick et al. (1986) Plant Cell Reports, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

While the present method has broad applicability, it is particularly useful in transforming plants which have been recalcitrant to known transformation methods. That is using the present method, maize elite lines, inbreds, and other lines difficult to transform can be transformed directly.

The following examples are offered by way of illustration and not by way of limitation.

EXPERIMENTAL

EXAMPLE I

Generation of a Monocot-Optimized Pat Gene

The PAT gene, which confers resistance to the herbicide glufosinate ammonium, was originally cloned from *Streptomyces viridochromogenes* (SEQ ID NO:1). The plasmid pB2/35SAcK consists of a synthetic plant-optimized PAT gene fused to a 35S-promoter and terminator cloned into pUC19. A second construct consisting of the PAT gene fused to a plant ubiquitin promoter was also utilized.

The PAT gene was first modified for expression in plants by replacing the GTG codon with ATG, and by modifying the four nucleotides upstream of the ATG codon to generate a plant-optimized PAT gene. The present invention relates to the further modification of the PAT gene to generate an example of a monocot-optimized selectable marker gene, the "monocot-optimized" PAT gene (moPAT). Analysis of the success of monocot-optimization was determined by recovery of transformants when the monocot-optimized PAT gene was used as a selectable marker, resulting in the isolation of a large number of highly herbicide-resistant events.

In order to generate a monocot-optimized form of the PAT gene, the preferred codon usage patterns for maize were examined. See, for example, Adang, U.S. Pat. No. 5,380,831. Information regarding the preferred codon usage of maize allowed for the replacement of codons with those codons that were more frequently used in maize. Codons were altered without altering the amino acid sequence of the PAT polypeptide. A codon usage table that reflects the codon usage of the monocot *Zea mays* was utilized to optimize the PAT gene expression in monocots, particularly maize. Because the codon usage among monocots is similar, the genes can be used in any monocot, for example, wheat. It is further recognized that monocot optimized sequences may express in acceptable levels in dicots.

The plant-optimized sequence of the PAT gene was translated and compared to the native protein sequence (SEQ ID NO:2). The protein sequence was then back-translated to nucleotide sequence using the above-described maize codon usage table. Modifications of the nucleotide sequence were not made if such modification would result in alteration of the amino acid sequence of the encoded PAT protein. The basic methodology utilized to generate the monocot-optimized PAT gene sequence (moPAT) is outlined below:

a. The PAT protein amino acid sequence (SEQ ID NO:2) was "back-translated" to obtain a nucleotide sequence having those codons most frequently used in maize. A nucleotide sequence having codons reflecting preferred codon usage patterns of maize and encoding the PAT protein was determined. The amino acid sequence (SEQ ID NO:4) of the protein encoded by the back-translated, modified "monocot-optimized" nucleotide sequence was identical to the amino acid sequence encoded by the native PAT nucleotide sequence (SEQ ID NO:2).

b. The nucleotide sequence was further modified by removal of regions of the gene including potential RNA processing sites, degradation sequences, and premature polyadenylation sequences.

c. Codons used <5% were avoided where possible.

d. The nucleotide sequence was further modified to delete clusters of A/T nucleotide pairs and G/C clusters having more than 10 G/C nucleotide pairs where possible. The GC content for maize genes is preferably 60–65% of the total nucleotide sequence.

e. Regions predicted to develop hairpin structures having a free energy of −12 kcal/mol were eliminated.

f. Cloning sites comprising a restriction enzyme recognition sequence may be added or removed.

g. Translation initiation sequence, based on a consensus from highly expressing maize genes (ACACGACACCatg), was added (SEQ ID NO:3).

Other factors, such as those that influence transcriptional or translational initiation sites, secondary structure of the gene or transcript, or result in modification of the poly(A) tail of the mRNA were additionally considered. A synthetic gene was then synthesized which incorporates such alterations and is shown in FIG. 1 (SEQ ID NO:3).

EXAMPLE II

Utilization of the moPAT Gene for Increased Transformation Efficiency

To confirm that the monocot-optimized gene was expressed in maize and produced a gene product in maize tissues, expression vectors containing the moPAT gene were transformed into maize cells or tissues. Several plasmids were generated in order to test the ability of the synthetic moPAT gene to function in a monocot-optimized fashion. Two separate methods were utilized in order to determine the efficiency and level of gene expression in monocots transformed with the monocot-optimized gene constructs. One method includes transformation of monocot cells with the monocot-optimized gene constructs followed by exposure of the cells to an herbicide (such as Bialaphos®, Basta, or glufosinate ammonium) to which the PAT gene is known to confer resistance. The number of colonies recovered following exposure to the herbicide is an indication of the ability of the monocot-optimized gene to function in maize tissues and cells. If transformation is benefited, a greater number of transformed events (herbicide-resistant colonies) would be recovered following transformation with the moPAT gene than following transformation with the PAT gene.

The data indicated that transformation of cells (comprising model or elite maize genotypes) with the I8092 (Ubi::moPAT) plasmid followed by selection on Bialaphos resulted in the generation of resistant calli. Such resistant colonies appear at an earlier time point and grow at a faster rate than those cells transformed with the PAT gene construct I6609. Furthermore, the data indicated that transformation of maize cells with the I8092 plasmid comprising the moPAT gene resulted in the isolation of a greater number of transformed events than transformation with the I6609 plasmid comprising the PAT gene (Tables 1 and 2).

TABLE 1

RESULTS OF TRANSFORMATIONS DONE WITH moPAT:

| Experiment | I6609 clones | I8092 (moPat) clones |
|---|---|---|
| 1 | 12 | 59 |
| 2 | 8 | 56 |
| 3 | 7 | 1 |
| 4 | 6 | 6 |
| 5 | 5 | 3 |
| 6 | 0 | 1 |
| 7 | 0 | 2 |
| Total: | 38 | 128 |

TABLE 2

| Experiment | Construct | # Plates Shot | # Resistant Calli | Frequency |
|---|---|---|---|---|
| 1 | 6609 | 42 | 800 | 19.0% |
| 2 | 6609 | 42 | 1006 | 23.4% |
| 3 | 8092 | 36 | 1140 | 31.7% |
| 4 | 8092 | 40 | 1116 | 27.9% |

A second approach that was utilized to determine the ability of the moPAT gene to direct expression of the moPAT gene product in maize was detection of the PAT gene product in extracts of maize tissues. A large number of events transformed with I8092 (Ubi::moPAT) were regenerated. Table 3 gives the results of these experiments using monocots derived from transformation with either the I6609 plasmid comprising the PAT gene or the I8092 plasmid comprising the moPAT gene (ELISA values reported at pg/μg protein). The data indicates that the PAT gene product is detected at greater than 200 pg/μg total soluble protein (tsp) in a larger proportion of events transformed with the moPAT gene as compared to events transformed with the PAT gene. The data further indicated that transformation with the moPAT gene results in the recovery of a greater number of herbicide-resistant transformed events than recovery following transformation with the PAT gene.

TABLE 3 moPAT ELISA RESULTS

| Construct | # Events Analyzed | Negative | 1–50 | 51–100 | >100 |
|---|---|---|---|---|---|
| 16609 | 46 | 20 | 12 | 6 | 8 |
| 18092 | 84 | 38 | 5 | 6 | 35 |

EXAMPLE III

Utilization of a Monocot-Optimized Gene for Increased Recovery of Events Transformed with a Non-Selectable Gene of Interest There is a need in the art to produce large numbers of transgenic events when developing transgenic crops. As demonstrated in the above-described example (Example II), a monocot-optimized gene may be utilized to increase recovery of transformed events following selection with a drug to which the monocot-optimized gene confers resistance. An important obstacle encountered by many skilled in the art is the inability to simply and accurately select for certain genes of interest. The moPAT gene functions in such a capacity, in that transformation of the moPAT gene with a gene of interest encoding a non-selectable gene product allows for selection of transformed events by selection of the transformed events in the present of a drug.

The gene encoding a nonselectable gene product may be encoded on the same plasmid comprising the moPAT gene or may be comprised within a separate plasmid or DNA molecule. If the gene of interest is provided on a separate plasmid, then it is likely, although not absolute, that the herbicide-resistant transformed events have been co-transfected with the non-selectable gene of interest, such as the cryIA(b) gene. Similarly, if the gene of interest resides on the same plasmid comprising the moPAT gene, then it is likely that herbicide-resistant events will comprise the gene of interest in addition to the moPAT gene. Therefore, by selection of transformed events using a drug to which the moPAT gene confers resistance, the probability of isolating a transformed event expressing the gene product of the gene of interest is increased. This is extremely important when producing transgenic crops in that large numbers of transgenic events must be isolated. Thus, the optimized gene enhances the ability to recover transformed events following transformation with a non-selectable gene of interest.

EXAMPLE IV

Transgenic Maize Comprising a Monocot-Optimized moPAT Gene

To provide a maize plant comprising a monocot-optimized gene, a transgenic maize plant is generated by transformation of a monocot-optimized gene into a maize regenerable tissue followed by regeneration of said regenerable tissue into a mature trangenic maize plant. The maize regenerable tissue is transformed with an expression vector comprising a monocot-optimized gene. Following regeneration of the mature maize plant, tissues of the transgenic plant are harvested and assayed for the presence of the monocot-optimized gene.

Monocot cells were transformed by methods known in the art. See, for example, Klein et al. (1988) *Proc. Natl. Acad. Sci. USA,* 85:4305–4309 and Klein et al. (1989) *Proc. Natl.*

Acad. Sci. USA, 86:6681–6685, herein incorporated by reference. Generally, GS3 callus lines were the target issue. GS3 is a high-type II (model) corn genotype. Generally, the callus was sieved in perparation for bombardment.

After being bombed with particles coated with DNA at a concentration of about 0.1 μg DNA/shot/plate, the tissue was maintained for two days on medium with no selection agent, afterwhich the tissue was transferred to medium with a selection agent (3 μg/liter bialophos) to initiate the plant regeneration process.

Expression of the moPAT gene and its gene product confers a selective advantage to the transgenic plant. Thus, a transgenic plant is generated that has a selective advantage (herbicide resistance) over a non-transgenic plant.

EXAMPLE V

Comparison of Transformation Efficiencies in Transgenic Wheat (PAT vs moPAT)

PAT and moPAT were transformed into the cultivar Bobwhite (wheat) in order to determine whether the monocot-optimized CAH sequence would lead to improved transformation efficiencies in other plant species besides maize. Two experiments were conducted comparing the transformation efficiencies of the PAT gene with moPAT. Heads were harvested 12–14 days post anthesis, seeds sterilized in 20% sodium hypochlorite for 30 min., and rinsed three times in sterile water. Immature embryos were excised and plated on MS salts, 2% sucrose, 150 mg/l asparagine, 0.5 mg/l thiamine HCl, 1.5 mg/l 2,4-D, pH 5.8, solidified with 2.5 g/l Gelrite (initiation medium). Plates were incubated in the dark at 26° C. Embryos were transferred, five days post excision, to the above medium supplemented with 0.4M mannitol and cultured for four hours, then bombarded with 1 micron gold particles (0.083 ug DNA, 650 psi).

Twenty hours post-bombardment, embryos were transferred from the high osmotic medium to initiation medium containing 3 mg/l Bialaphos and cultured in the dark (16/8 photo-period). The embryos were subcultured approximately every 2 weeks for 4 months. Resistant calli were placed initially on regeneration media (MS salts and vitamins, 2% sucrose, 0.5 mg/l Dicamba, 3 mg/l Bialaphos, 2.5 mg/l Gelrite), and upon shoot formation, transferred to the same medium (minus Dicamba) containing 5 mg/l Zeatin and transferred to light. Shoots were rooted in MS salts and vitamins at concentrations of 0.1 g/l myo-inositol, 4% sucrose, 0.7 mg/l IBA, 0.3 mg/l NAA, 1.5 g/l Gelrite. The transformation efficiency for the moPAT construct was triple that of PAT. The transformation efficiency for PAT was 0.3% and for moPAT was 0.9%, as is shown in Table 4.

TABLE 4

PAT vs. moPAT TRANSFORMATION EFFICIENCY

| Gene | Dp # | # Embryos | # PCR+ Events | # PCR+ Events with seed | Trans. Efficiency |
|---|---|---|---|---|---|
| PAT | 6609 | 625 | 4 | 2 | 0.3% |
| moPAT | 8092 | 568 | 6 | 5 | 0.9% |

EXAMPLE VI

Generation of a Monocot-Optimized CAH Sequence

Cyanamide in aqueous solution or in the form of its calcium salt is used as a fertilizer in agriculture. It also can act as an effective herbicide if applied prior to sowing. The enzyme cyanamide hydratase hydrates the nitrile group of cyanamide to form urea.

Cyanamide hydratase has been purified from *Myrothecium verrucaria*. See, Maier-Greiner et al. (1991) *Proc. Natl. Acad. Sci. USA*, 88:4260–4264, herein incorporated by reference. For the nucleotide and amino acid sequence of the native cyanamide hydratase see SEQ ID NOS 5 & 6 respectively. The gene encoding cyanamide hydratase was optimized for expression in maize by the methods outlines above. Codons were altered without altering the amino acid sequence of the enzyme. The nucleic acid and amino acid sequences of the optimized gene are given in FIG. 2 (SEQ ID NOS 7 & 8, respectively).

EXAMPLE VII

Analysis of T1 Progeny of moCAH Transgenic Events

To characterize the stability of the moCAH selectable marker from parent to progeny, maize cells were transformed with moCAH and successive generations were assayed for the presence of the moCAH gene. Three transgenic events were produced using the monocot-optimized cyanamide hydratase gene (moCAH) as the selectable marker. These events were confirmed at T0 plant level by Southern blot analysis. In order to confirm transgene inheritance in these events T1 plants were analyzed for the presence of the transgene using PCR and herbicide leaf painting techniques. Seeds were planted in soil in the greenhouse and plants were sampled at V4–5 leaf stage. In the first transgenic event thirty-nine T1 plants from one T0 plant were analyzed by PCR of which twenty five T1 plants were positive for the moCAH transgene. In the second transgenic event, two T0 plants were used. Fifty nine T1 plants from the first T0 were analyzed by PCR, of which thirty two were positive for the moCAH transgene. Out of fourteen T1 plants from the second T0 plant, eight T1 plants were positive for the moCAH transgene. None of the seventy-one T1 seeds germinated in the third transgenic event due to poor seed quality and mold problems.

To find out whether the inherited moCAH gene was still functional, T1 plants at V5–6 stage were leaf-painted with a 10% solution of the commercial herbicide Dormex (containing 50% cyanamide). All control non-transformed plants were susceptible to the herbicide with the painted leaf showing severe damage. Some transgenic T1 plants from both transgenic events were completely resistant to 50% cyanamide demonstrating no damage from leaf painting. In Event #2, PCR analysis showing the presence of the moCAH transgene and leaf painting results demonstrating improved resistance to cyanamide displayed a segregation pattern of approximately 1:1. These results clearly demonstrate that the moCAH gene can be used efficiently as a selectable marker to transform maize plants and that the introduced moCAH gene can be stably integrated into the maize genome and transmitted to the following generation. The DNA construct that contained the moCAH gene was arranged on the integrating vector 10675 in the order Ubi promoter;; moCAH gene;; PinII terminator. Sequences of the primers used for PCR confirmation of moCAH presence in the plant genome are given below.

primer 1 (SEQ ID NO:9): CTACAACCACTCCAT-GCGCGTGTTC primer 2 (SEQ ID NO:10): CACATAACACA-CAACTTTGATGCCCAC

EXAMPLE VIII

Comparison of Transformation Efficiencies in Transgenic Wheat (CAH vs. moCAH)

To test whether the use of moCAH improved the transformation efficiency in other species, both CAH and moCAH were transformed into the wheat cultivar (Bobwhite). Four experiments were conducted to test CAH against moCAH transformation efficiency. Media used were as described above except that 37.5 mg/l cyanamide was substituted for Bialaphos. No selection agent was used in the regeneration and rooting stages. The results showed a 0.0% transformation efficiency for CAH and a 0.8% transformation efficiency for moCAH.

TABLE 5

CAH vs. moCAH TRANSFORMATION EFFICIENCY

| Gene | Dp # | # Embryos | # PCR+ Events | # PCR+ Events with seed | Trans. Efficiency |
| --- | --- | --- | --- | --- | --- |
| CAH | 10660 | 652 | 0 | 0 | 0% |
| moCAH | 10675 | 653 | 5 | 5 | 0.8% |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A plant which has been transformed with a gene comprising the nucleotide sequence set forth in SEQ ID NO: 3.

2. A plant which has been transformed with a gene comprising the nucleotide sequence set forth in SEQ ID NO: 7.

3. Transformed seed from the plant of claim 1.

4. Transformed seed from the plant of claim 2.

5. A gene comprising the nucleotide sequence set forth in SEQ ID NO: 3.

6. A gene comprising the nucleotide sequence set forth in SEQ ID NO: 7.

7. The plant of claim 1 wherein said plant is a monocot.

8. The plant of claim 7 wherein said monocot is maize or wheat.

9. The plant of claim 2 wherein said plant is a monocot.

10. The plant of claim 9 wherein said monocot is maize or wheat.

* * * * *

SEQUENCE LISTING

<160> NUMBER OF SEQ ID NOS: 10

<210> SEQ ID NO 1
<211> LENGTH: 552
<212> TYPE: DNA
<213> ORGANISM: Streptomyces viridochromogenes
<220> FEATURE:
<221> NAME/KEY: CDS
<222> LOCATION: (01)..(549)

<400> SEQUENCE: 1

```
atg tct ccg gag agg aga cca gtt gag att agg cca gct aca gca gct        48
Met Ser Pro Glu Arg Arg Pro Val Glu Ile Arg Pro Ala Thr Ala Ala
 1               5                  10                  15 gat atg gcc gcg gtt tgt gat atc gtt aac cat tac att gag acg tct        96
Asp Met Ala Ala Val Cys Asp Ile Val Asn His Tyr Ile Glu Thr Ser
                20                  25                  30 aca gtg aac ttt agg aca gag cca caa aca cca caa gag tgg att gat       144
Thr Val Asn Phe Arg Thr Glu Pro Gln Thr Pro Gln Glu Trp Ile Asp
             35                  40                  45 gat cta gag agg ttg caa gat aga tac cct tgg ttg gtt gct gag gtt       192
Asp Leu Glu Arg Leu Gln Asp Arg Tyr Pro Trp Leu Val Ala Glu Val
 50                  55                  60 gag ggt gtt gtg gct ggt att gct tac gct ggg ccc tgg aag gct agg       240
Glu Gly Val Val Ala Gly Ile Ala Tyr Ala Gly Pro Trp Lys Ala Arg
 65                  70                  75                  80 aac gct tac gat tgg aca gtt gag agt act gtt tac gtg tca cat agg       288
Asn Ala Tyr Asp Trp Thr Val Glu Ser Thr Val Tyr Val Ser His Arg
                 85                  90                  95 cat caa agg ttg ggc cta gga tcc aca ttg tac aca cat ttg ctt aag       336
His Gln Arg Leu Gly Leu Gly Ser Thr Leu Tyr Thr His Leu Leu Lys
                100                 105                 110 tct atg gag gcg caa ggt ttt aag tct gtg gtt gct gtt ata ggc ctt       384
Ser Met Glu Ala Gln Gly Phe Lys Ser Val Val Ala Val Ile Gly Leu
            115                 120                 125
```

```
cca aac gat cca tct gtt agg ttg cat gag gct ttg gga tac aca gcc    432
Pro Asn Asp Pro Ser Val Arg Leu His Glu Ala Leu Gly Tyr Thr Ala
    130                 135                 140 cgg ggt aca ttg cgc gca gct gga tac aag cat ggt gga tgg cat gat    480
Arg Gly Thr Leu Arg Ala Ala Gly Tyr Lys His Gly Gly Trp His Asp
145                 150                 155                 160 gtt ggt ttt tgg caa agg gat ttt gag ttg cca gct cct cca agg cca    528
Val Gly Phe Trp Gln Arg Asp Phe Glu Leu Pro Ala Pro Pro Arg Pro
                165                 170                 175 gtt agg cca gtt acc cag atc tga                                    552
Val Arg Pro Val Thr Gln Ile
            180

<210> SEQ ID NO 2
<211> LENGTH: 183
<212> TYPE: PRT
<213> ORGANISM: Streptomyces viridochromogenes

<400> SEQUENCE: 2

Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
                20                  25                  30

Thr Val Asn Phe Arg Thr Glu Pro Gln Thr Pro Gln Glu Trp Ile Asp
            35                  40                  45

Asp Leu Glu Arg Leu Gln Asp Arg Tyr Pro Trp Leu Val Ala Glu Val
        50                  55                  60

Glu Gly Val Val Ala Gly Ile Ala Tyr Ala Gly Pro Trp Lys Ala Arg
65                  70                  75                  80

Asn Ala Tyr Asp Trp Thr Val Glu Ser Thr Val Tyr Val Ser His Arg
                85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
        115                 120                 125

Pro Asn Asp Pro Ser Val Arg Leu His Glu Ala Leu Gly Tyr Thr Ala
    130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
            180

<210> SEQ ID NO 3
<211> LENGTH: 552
<212> TYPE: DNA
<213> ORGANISM: Streptomyces viridochromogenes
<220> FEATURE:
<221> NAME/KEY: CDS
<222> LOCATION: (01)..(549)

<400> SEQUENCE: 3 atg tcc ccc gag cgc cgc ccc gtc gag atc cgc ccg gcc acc gcc gcc    48
Met Ser Pro Glu Arg Arg Pro Val Glu Ile Arg Pro Ala Thr Ala Ala
1               5                   10                  15 gac atg gcc gcc gtg tgc gac atc gtg aac cac tac atc gag acc tcc    96
Asp Met Ala Ala Val Cys Asp Ile Val Asn His Tyr Ile Glu Thr Ser
                20                  25                  30
```

-continued

```
acc gtg aac ttc cgc acc gag ccg cag acc ccg cag gag tgg atc gac       144
Thr Val Asn Phe Arg Thr Glu Pro Gln Thr Pro Gln Glu Trp Ile Asp
        35                  40                  45 gac ctg gag cgc ctc cag gac cgc tac ccg tgg ctc gtg gcc gag gtg       192
Asp Leu Glu Arg Leu Gln Asp Arg Tyr Pro Trp Leu Val Ala Glu Val
 50                  55                  60 gag ggc gtg gtg gcc ggc atc gcc tac gcc ggc ccg tgg aag gcc cgc       240
Glu Gly Val Val Ala Gly Ile Ala Tyr Ala Gly Pro Trp Lys Ala Arg
 65                  70                  75                  80 aac gcc tac gac tgg acc gtg gag tcc acc gtg tac gtg tcc cac cgc       288
Asn Ala Tyr Asp Trp Thr Val Glu Ser Thr Val Tyr Val Ser His Arg
                 85                  90                  95 cac cag cgc ctc ggc ctc ggc tcc acc ctc tac acc cac ctc ctc aag       336
His Gln Arg Leu Gly Leu Gly Ser Thr Leu Tyr Thr His Leu Leu Lys
            100                 105                 110 agc atg gag gcc cag ggc ttc aag tcc gtg gtg gcc gtg atc ggc ctc       384
Ser Met Glu Ala Gln Gly Phe Lys Ser Val Val Ala Val Ile Gly Leu
        115                 120                 125 ccg aac gac ccg tcc gtg cgc ctc cac gag gcc ctc ggc tac acc gcc       432
Pro Asn Asp Pro Ser Val Arg Leu His Glu Ala Leu Gly Tyr Thr Ala
130                 135                 140 cgc ggc acc ctc cgc gcc gcc ggc tac aag cac ggc ggc tgg cac gac       480
Arg Gly Thr Leu Arg Ala Ala Gly Tyr Lys His Gly Gly Trp His Asp
145                 150                 155                 160 gtc ggc ttc tgg cag cgc gac ttc gag ctg ccg gcc ccg cgc ccg           528
Val Gly Phe Trp Gln Arg Asp Phe Glu Leu Pro Ala Pro Arg Pro
                 165                 170                 175 gtg cgc ccg gtg acg cag atc tga                                       552
Val Arg Pro Val Thr Gln Ile
            180
```

<210> SEQ ID NO 4
<211> LENGTH: 183
<212> TYPE: PRT
<213> ORGANISM: Streptomyces viridochromogenes

<400> SEQUENCE: 4

```
Met Ser Pro Glu Arg Arg Pro Val Glu Ile Arg Pro Ala Thr Ala Ala
 1               5                  10                  15

Asp Met Ala Ala Val Cys Asp Ile Val Asn His Tyr Ile Glu Thr Ser
            20                  25                  30

Thr Val Asn Phe Arg Thr Glu Pro Gln Thr Pro Gln Glu Trp Ile Asp
        35                  40                  45

Asp Leu Glu Arg Leu Gln Asp Arg Tyr Pro Trp Leu Val Ala Glu Val
 50                  55                  60

Glu Gly Val Val Ala Gly Ile Ala Tyr Ala Gly Pro Trp Lys Ala Arg
 65                  70                  75                  80

Asn Ala Tyr Asp Trp Thr Val Glu Ser Thr Val Tyr Val Ser His Arg
                 85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
        115                 120                 125

Pro Asn Asp Pro Ser Val Arg Leu His Glu Ala Leu Gly Tyr Thr Ala
130                 135                 140

Arg Gly Thr Leu Arg Ala Ala Gly Tyr Lys His Gly Gly Trp His Asp
145                 150                 155                 160
```

-continued

```
Val Gly Phe Trp Gln Arg Asp Phe Glu Leu Pro Ala Pro Pro Arg Pro
            165                 170                 175
Val Arg Pro Val Thr Gln Ile
            180

<210> SEQ ID NO 5
<211> LENGTH: 735
<212> TYPE: DNA
<213> ORGANISM: Myrothecium verrucaria
<220> FEATURE:
<221> NAME/KEY: CDS
<222> LOCATION: (01)..(732)

<400> SEQUENCE: 5 atg tct tct tca gaa gtc aaa gcc aac gga tgg act gcc gtt cca gtc      48
Met Ser Ser Ser Glu Val Lys Ala Asn Gly Trp Thr Ala Val Pro Val
 1               5                  10                  15 agc gca aag gcc att gtt gac tcc ctg gga aag ctt ggt gat gtc tcc      96
Ser Ala Lys Ala Ile Val Asp Ser Leu Gly Lys Leu Gly Asp Val Ser
                20                  25                  30 tca tat tct gtg gaa gat atc gcg ttc cct gcg gca gac aaa ctt gtt     144
Ser Tyr Ser Val Glu Asp Ile Ala Phe Pro Ala Ala Asp Lys Leu Val
            35                  40                  45 gcc gag gca cag gcc ttt gtg aag gcc cga ttg agt ccc gaa acc tac     192
Ala Glu Ala Gln Ala Phe Val Lys Ala Arg Leu Ser Pro Glu Thr Tyr
        50                  55                  60 aat cac tcc atg cgc gtt ttc tac tgg gga acc gtc atc gcg aga cgt     240
Asn His Ser Met Arg Val Phe Tyr Trp Gly Thr Val Ile Ala Arg Arg
 65                  70                  75                  80 tta ctt ccc gag caa gct aaa gac ttg tct cca agt aca tgg gca ctg     288
Leu Leu Pro Glu Gln Ala Lys Asp Leu Ser Pro Ser Thr Trp Ala Leu
                85                  90                  95 aca tgt ctt ctg cat gac gtt ggt act gcg gag gca tac ttt aca tct     336
Thr Cys Leu Leu His Asp Val Gly Thr Ala Glu Ala Tyr Phe Thr Ser
                100                 105                 110 aca cga atg tcc ttc gat att tac ggt ggc att aag gct atg gag gtg     384
Thr Arg Met Ser Phe Asp Ile Tyr Gly Gly Ile Lys Ala Met Glu Val
            115                 120                 125 ctc aag gtc ctt ggg agt agc acc gac cag gct gag gct gtt gcc gag     432
Leu Lys Val Leu Gly Ser Ser Thr Asp Gln Ala Glu Ala Val Ala Glu
    130                 135                 140 gcc atc att cgt cat gag gat gtg ggg gta gat ggc aac atc aca ttc     480
Ala Ile Ile Arg His Glu Asp Val Gly Val Asp Gly Asn Ile Thr Phe
145                 150                 155                 160 ctc ggt cag ttg atc cag ctg gct acg ctt tat gac aat gtc ggg gcc     528
Leu Gly Gln Leu Ile Gln Leu Ala Thr Leu Tyr Asp Asn Val Gly Ala
                165                 170                 175 tac gat ggg att gat gat ttt ggt agc tgg gtt gat gac acc aca cgc     576
Tyr Asp Gly Ile Asp Asp Phe Gly Ser Trp Val Asp Asp Thr Thr Arg
            180                 185                 190 aac agt atc aac acg gca ttc cca cga cat ggt tgg tgt tct tgg ttt     624
Asn Ser Ile Asn Thr Ala Phe Pro Arg His Gly Trp Cys Ser Trp Phe
        195                 200                 205 gcc tgc acg gtt cgt aag gaa gaa agt aac aag cct tgg tgc cac aca     672
Ala Cys Thr Val Arg Lys Glu Glu Ser Asn Lys Pro Trp Cys His Thr
    210                 215                 220 acg cat atc cct cag ttc gat aaa cag atg gaa gcg aac act ttg atg     720
Thr His Ile Pro Gln Phe Asp Lys Gln Met Glu Ala Asn Thr Leu Met
225                 230                 235                 240 aag cct tgg gag taa                                                   735
Lys Pro Trp Glu
```

-continued

<210> SEQ ID NO 6
<211> LENGTH: 244
<212> TYPE: PRT
<213> ORGANISM: Myrothecium verrucaria

<400> SEQUENCE: 6

Met Ser Ser Ser Glu Val Lys Ala Asn Gly Trp Thr Ala Val Pro Val
1               5                   10                  15

Ser Ala Lys Ala Ile Val Asp Ser Leu Gly Lys Leu Gly Asp Val Ser
            20                  25                  30

Ser Tyr Ser Val Glu Asp Ile Ala Phe Pro Ala Ala Asp Lys Leu Val
        35                  40                  45

Ala Glu Ala Gln Ala Phe Val Lys Ala Arg Leu Ser Pro Glu Thr Tyr
    50                  55                  60

Asn His Ser Met Arg Val Phe Tyr Trp Gly Thr Val Ile Ala Arg Arg
65                  70                  75                  80

Leu Leu Pro Glu Gln Ala Lys Asp Leu Ser Pro Ser Thr Trp Ala Leu
                85                  90                  95

Thr Cys Leu Leu His Asp Val Gly Thr Ala Glu Ala Tyr Phe Thr Ser
            100                 105                 110

Thr Arg Met Ser Phe Asp Ile Tyr Gly Gly Ile Lys Ala Met Glu Val
        115                 120                 125

Leu Lys Val Leu Gly Ser Ser Thr Asp Gln Ala Glu Ala Val Ala Glu
    130                 135                 140

Ala Ile Ile Arg His Glu Asp Val Gly Val Asp Gly Asn Ile Thr Phe
145                 150                 155                 160

Leu Gly Gln Leu Ile Gln Leu Ala Thr Leu Tyr Asp Asn Val Gly Ala
                165                 170                 175

Tyr Asp Gly Ile Asp Asp Phe Gly Ser Trp Val Asp Asp Thr Thr Arg
            180                 185                 190

Asn Ser Ile Asn Thr Ala Phe Pro Arg His Gly Trp Cys Ser Trp Phe
        195                 200                 205

Ala Cys Thr Val Arg Lys Glu Glu Ser Asn Lys Pro Trp Cys His Thr
    210                 215                 220

Thr His Ile Pro Gln Phe Asp Lys Gln Met Glu Ala Asn Thr Leu Met
225                 230                 235                 240

Lys Pro Trp Glu

<210> SEQ ID NO 7
<211> LENGTH: 735
<212> TYPE: DNA
<213> ORGANISM: Myrothecium verrucaria
<220> FEATURE:
<221> NAME/KEY: CDS
<222> LOCATION: (01)..(732)

<400> SEQUENCE: 7 atg tcg tcc tcc gag gtg aag gcc aac ggc tgg acc gcg gtc ccc gtc     48
Met Ser Ser Ser Glu Val Lys Ala Asn Gly Trp Thr Ala Val Pro Val
1               5                   10                  15 agc gcc aag gcc atc gtg gac tcc ctc ggc aag ctc ggc gac gtc agc     96
Ser Ala Lys Ala Ile Val Asp Ser Leu Gly Lys Leu Gly Asp Val Ser
            20                  25                  30 tcc tac tcc gtg gag gac atc gcc ttc cca gcg gcc gac aag ctc gtg    144
Ser Tyr Ser Val Glu Asp Ile Ala Phe Pro Ala Ala Asp Lys Leu Val
        35                  40                  45

```
gcc gag gcc cag gcg ttc gtc aag gcc cgc ctc tcc ccg gag acc tac      192
Ala Glu Ala Gln Ala Phe Val Lys Ala Arg Leu Ser Pro Glu Thr Tyr
 50                  55                  60 aac cac tcc atg cgc gtg ttc tac tgg ggc acc gtg atc gcc agg agg      240
Asn His Ser Met Arg Val Phe Tyr Trp Gly Thr Val Ile Ala Arg Arg
 65                  70                  75                  80 ctc ctc ccg gag cag gcc aag gac ctc tcc ccg tcc acc tgg gcc ctc      288
Leu Leu Pro Glu Gln Ala Lys Asp Leu Ser Pro Ser Thr Trp Ala Leu
                 85                  90                  95 acc tgc ctc ctc cac gac gtg ggc acc gcc gag gcc tac ttc acc tcc      336
Thr Cys Leu Leu His Asp Val Gly Thr Ala Glu Ala Tyr Phe Thr Ser
                100                 105                 110 acc cgc atg tcc ttc gac atc tac ggc ggc atc aag gcg atg gag gtc      384
Thr Arg Met Ser Phe Asp Ile Tyr Gly Gly Ile Lys Ala Met Glu Val
                        115                 120                 125 ctc aag gtg ctc ggc tcc tcc acc gac cag gcg gag gcg gtg gcc gag      432
Leu Lys Val Leu Gly Ser Ser Thr Asp Gln Ala Glu Ala Val Ala Glu
130                 135                 140 gcc atc atc cgc cac gag gac gtc ggc gtc gac ggc aac atc acc ttc      480
Ala Ile Ile Arg His Glu Asp Val Gly Val Asp Gly Asn Ile Thr Phe
145                 150                 155                 160 ctc ggc cag ctc atc cag ctc gcc acc ctc tac gac aac gtg ggc gcc      528
Leu Gly Gln Leu Ile Gln Leu Ala Thr Leu Tyr Asp Asn Val Gly Ala
                        165                 170                 175 tac gac ggc atc gac gac ttc ggc tcc tgg gtg gac gac acc acc cgc      576
Tyr Asp Gly Ile Asp Asp Phe Gly Ser Trp Val Asp Asp Thr Thr Arg
                180                 185                 190 aac tcc atc aac acc gcc ttc ccg cgc cac ggc tgg tgc tcc tgg ttc      624
Asn Ser Ile Asn Thr Ala Phe Pro Arg His Gly Trp Cys Ser Trp Phe
            195                 200                 205 gcc tgc acc gtg cgc aag gag gag tcc aac aag ccg tgg tgc cac acc      672
Ala Cys Thr Val Arg Lys Glu Glu Ser Asn Lys Pro Trp Cys His Thr
210                 215                 220 acc cac atc ccg cag ttc gac aag cag atg gag gcc aac acc ctg atg      720
Thr His Ile Pro Gln Phe Asp Lys Gln Met Glu Ala Asn Thr Leu Met
225                 230                 235                 240 aag ccg tgg gag tga                                                  735
Lys Pro Trp Glu <210> SEQ ID NO 8
<211> LENGTH: 244
<212> TYPE: PRT
<213> ORGANISM: Myrothecium verrucaria

<400> SEQUENCE: 8

Met Ser Ser Ser Glu Val Lys Ala Asn Gly Trp Thr Ala Val Pro Val
  1               5                  10                  15

Ser Ala Lys Ala Ile Val Asp Ser Leu Gly Lys Leu Gly Asp Val Ser
                 20                  25                  30

Ser Tyr Ser Val Glu Asp Ile Ala Phe Pro Ala Ala Asp Lys Leu Val
             35                  40                  45

Ala Glu Ala Gln Ala Phe Val Lys Ala Arg Leu Ser Pro Glu Thr Tyr
         50                  55                  60

Asn His Ser Met Arg Val Phe Tyr Trp Gly Thr Val Ile Ala Arg Arg
 65                  70                  75                  80

Leu Leu Pro Glu Gln Ala Lys Asp Leu Ser Pro Ser Thr Trp Ala Leu
                 85                  90                  95

Thr Cys Leu Leu His Asp Val Gly Thr Ala Glu Ala Tyr Phe Thr Ser
                100                 105                 110
```

```
Thr Arg Met Ser Phe Asp Ile Tyr Gly Gly Ile Lys Ala Met Glu Val
        115                 120                 125

Leu Lys Val Leu Gly Ser Ser Thr Asp Gln Ala Glu Ala Val Ala Glu
        130                 135                 140

Ala Ile Ile Arg His Glu Asp Val Gly Val Asp Gly Asn Ile Thr Phe
145                 150                 155                 160

Leu Gly Gln Leu Ile Gln Leu Ala Thr Leu Tyr Asp Asn Val Gly Ala
                165                 170                 175

Tyr Asp Gly Ile Asp Asp Phe Gly Ser Trp Val Asp Asp Thr Thr Arg
            180                 185                 190

Asn Ser Ile Asn Thr Ala Phe Pro Arg His Gly Trp Cys Ser Trp Phe
        195                 200                 205

Ala Cys Thr Val Arg Lys Glu Glu Ser Asn Lys Pro Trp Cys His Thr
    210                 215                 220

Thr His Ile Pro Gln Phe Asp Lys Gln Met Glu Ala Asn Thr Leu Met
225                 230                 235                 240

Lys Pro Trp Glu
```

<210> SEQ ID NO 9
<211> LENGTH: 25
<212> TYPE: DNA
<213> ORGANISM: Myrothecium verrucaria
<220> FEATURE:
<223> OTHER INFORMATION: Synthetic Oligonucleotide for moCAH detection

<400> SEQUENCE: 9
ctacaaccac tccatgcgcg tgttc                                    25

<210> SEQ ID NO 10
<211> LENGTH: 27
<212> TYPE: DNA
<213> ORGANISM: Myrothecium verrucaria
<220> FEATURE:
<223> OTHER INFORMATION: Synthetic Oligonucleotide for moCAH detection

<400> SEQUENCE: 10
cacataacac acaactttga tgcccac                                  27